United States Patent
Rickard

(10) Patent No.: US 8,527,055 B2
(45) Date of Patent: Sep. 3, 2013

(54) APPLICATION OF AN ELECTRICAL FIELD IN THE VICINITY OF THE TRABECULAR MESHWORK TO TREAT GLAUCOMA

(75) Inventor: Matthew J. A. Rickard, Tustin, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 637 days.

(21) Appl. No.: 12/508,104

(22) Filed: Jul. 23, 2009

(65) Prior Publication Data

US 2011/0022118 A1   Jan. 27, 2011

(51) Int. Cl.
*A61N 1/00*    (2006.01)
*A61B 17/56*   (2006.01)

(52) U.S. Cl.
USPC .............................. 607/53; 607/141

(58) Field of Classification Search
USPC ...................... 607/53, 141; 606/41
See application file for complete search history.

(56) References Cited

U.S. PATENT DOCUMENTS

| | | |
|---|---|---|
| 4,603,697 A | 8/1986 | Kamerling |
| 5,005,577 A | 4/1991 | Frenkel |
| 6,712,764 B2 | 3/2004 | Jeffries et al. |
| 6,749,568 B2 | 6/2004 | Fleischman et al. |
| 7,169,106 B2 | 1/2007 | Fleischman et al. |
| 7,252,006 B2 | 8/2007 | Tai et al. |
| 2002/0013572 A1* | 1/2002 | Berlin ............................ 606/4 |
| 2004/0106951 A1 | 6/2004 | Edman et al. |
| 2004/0116794 A1 | 6/2004 | Fink et al. |

FOREIGN PATENT DOCUMENTS

| | | |
|---|---|---|
| WO | WO 02/056805 A2 | 7/2002 |
| WO | WO 02/056805 A3 | 7/2002 |

OTHER PUBLICATIONS

"Intraocular Pressure Sensor: Where Are We—Where Will We Go?"; Journal Graefe's Archive for Clinical and Experimental Ophthalmology; Publisher Springer Berlin/Heidelberg; ISSN 0721-832X (Print) 1435-702X (Online); Issue vol. 240; No. 5/May 2002; DOI 10.1007/s00417-002-0474-y; pp. 335-336; Subject Collection Medicine.
"How Does Nonpenetrating Glaucoma Surgery Work? Aqueous Outflow Resistance and Glaucoma Surgery"; Douglas H. Johnson, MD and Mark Johnson PhD; Journal of Glaucoma 10:55-67; 2001 Lippincott Williams & Wilkins, Inc.

* cited by examiner

*Primary Examiner* — Nicole F Lavert
(74) *Attorney, Agent, or Firm* — Kenneth Bassinger

(57) ABSTRACT

The present invention is a method of treating glaucoma by applying an electric field in the vicinity of the juxtacanalicular region of the trabecular meshwork sufficient to cause migration or reorientation of glycosaminoglycans located in the extracellular matrix. A device for applying the electric field includes a controller coupled to a pressure sensor, and a pair of electrodes coupled to a voltage source. The electrodes apply the electric field, and the controller controls the application of the electric field based on IOP measurements from the pressure sensor.

4 Claims, 2 Drawing Sheets

APPLICATION OF AN ELECTRICAL FIELD IN THE VICINITY OF THE TRABECULAR MESHWORK TO TREAT GLAUCOMA

BACKGROUND OF THE INVENTION

The present invention relates to a treatment for glaucoma and more particular to a method and apparatus for applying an electrical field in the vicinity of the trabecular meshwork to manipulate glycosaminoglycans in the trabecular meshwork.

Glaucoma, a group of eye diseases affecting the retina and optic nerve, is one of the leading causes of blindness worldwide. Glaucoma results when the intraocular pressure (IOP) increases to pressures above normal for prolonged periods of time. IOP can increase due to an imbalance of the production of aqueous and the drainage of the aqueous. Left untreated, an elevated IOP causes irreversible damage the optic nerve and retinal fibers resulting in a progressive, permanent loss of vision.

The eye's ciliary body constantly produces aqueous, the clear fluid that fills the anterior chamber of the eye. The aqueous flows out of the anterior chamber through a complex drainage system. The balance between the production and drainage of aqueous determines the eye's IOP.

Open angle (also called chronic open angle or primary open angle) is the most common type of glaucoma. With this type, even though the anterior structures of the eye appear normal, aqueous fluid builds within the anterior chamber, causing the IOP to become elevated. Left untreated, this may result in permanent damage of the optic nerve and retina. Eye drops are generally prescribed to lower IOP. In some cases, surgery is performed if the IOP cannot be adequately controlled with medical therapy.

Only about 10% of the glaucoma population suffers from acute angle closure glaucoma. Acute angle closure occurs because of an abnormality of the structures in the front of the eye. In most of these cases, the space between the iris and cornea is more narrow than normal, leaving a smaller channel for the aqueous to pass through. If the flow of aqueous becomes completely blocked, the IOP rises sharply, causing a sudden angle closure attack.

Secondary glaucoma occurs as a result of another disease or problem within the eye such as: inflammation, trauma, previous surgery, diabetes, tumor, and certain medications. For this type, both the glaucoma and the underlying problem must be treated.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior chamber of the eye includes the structures that cause glaucoma. Aqueous fluid is produced by the ciliary bodies 140 that lie beneath the iris 130 and adjacent to the lens 110 in the anterior chamber. This aqueous washes over the lens 110 and iris 130 and flows to the drainage system located in the angle of the anterior chamber. The angle of the anterior chamber, which extends circumferentially around the eye, contains structures that allow the aqueous to drain. The first structure, and the one most commonly implicated in glaucoma, is the trabecular meshwork 150. The trabecular meshwork 150 extends circumferentially around the anterior chamber in the angle. The trabecular meshwork 150 seems to act as a filter, limiting the outflow of aqueous and providing a back pressure producing the IOP. Schlemm's canal 160 is located beyond the trabecular meshwork 150. Schlemm's canal 160 has collector channels that lead to aqueous veins that allow aqueous to flow out of the anterior chamber. The two arrows in the anterior chamber of FIG. 1 show the flow of aqueous from the ciliary bodies 140, over the lens 110, over the iris 130, through the trabecular meshwork 150, and into Schlemm's canal 160 and its collector channels.

Glaucoma is treated most commonly with eye drops. When eye drops prove ineffective, surgical intervention may be necessary. Currently, there are a variety of invasive surgical procedures that are used to treat glaucoma. Most of these procedures subject the patient to an incision in the eye that can lead to complications. Accordingly, a treatment that does not involve an incision would be beneficial.

The present invention provides a method and device for applying an electric field in the vicinity of the juxtacanalicular region of the trabecular meshwork sufficient to cause the glycosaminoglycans in the extracellular matrix to migrate and/or reorient thereby reducing the resistance to aqueous outflow through the trabecular meshwork.

SUMMARY OF THE INVENTION

In one embodiment consistent with the principles of the present invention, the present invention is a method of treating glaucoma by applying an electric field in the vicinity of the juxtacanalicular region of the trabecular meshwork sufficient to cause migration or reorientation of glycosaminoglycans located in the extracellular matrix.

In another embodiment consistent with the principles of the present invention, the present invention is a method treating glaucoma comprising providing a pair of electrodes coupled to a voltage source; placing the pair of electrodes in the vicinity of the juxtacanalicular region of the trabecular meshwork; and applying a voltage across the pair of electrodes sufficient to cause migration or reorientation of glycosaminoglycans located in the extracellular matrix.

In another embodiment consistent with the principles of the present invention, the present invention is a device for applying an electric filed in the vicinity of the juxtacanalicular region of the trabecular meshwork. The device has a pair of electrodes configured to apply an electric field in the vicinity of the trabecular meshwork. The pair of electrodes is coupled to a voltage source. A controller applies the electric field to the juxtacanalicular region of the trabecular meshwork.

In another embodiment consistent with the principles of the present invention, the present invention is a device for applying an electric filed in the vicinity of the juxtacanalicular region of the trabecular meshwork. The device has a pair of electrodes configured to apply an electric field in the vicinity of the trabecular meshwork. The pair of electrodes is coupled to a voltage source. A pressure senor is coupled to a controller. The controller applies the electric field to the juxtacanalicular region of the trabecular meshwork. The controller uses IOP readings from the pressure sensor to control the applied electric field.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
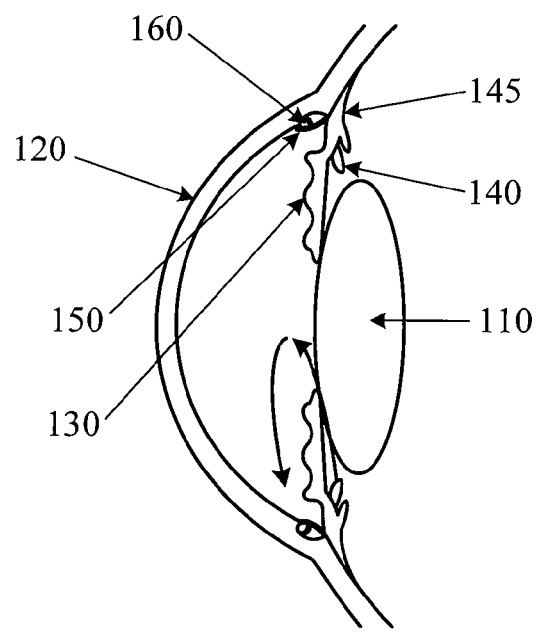
FIG. 1 is a diagram of the front portion of an eye.
Figure 2:
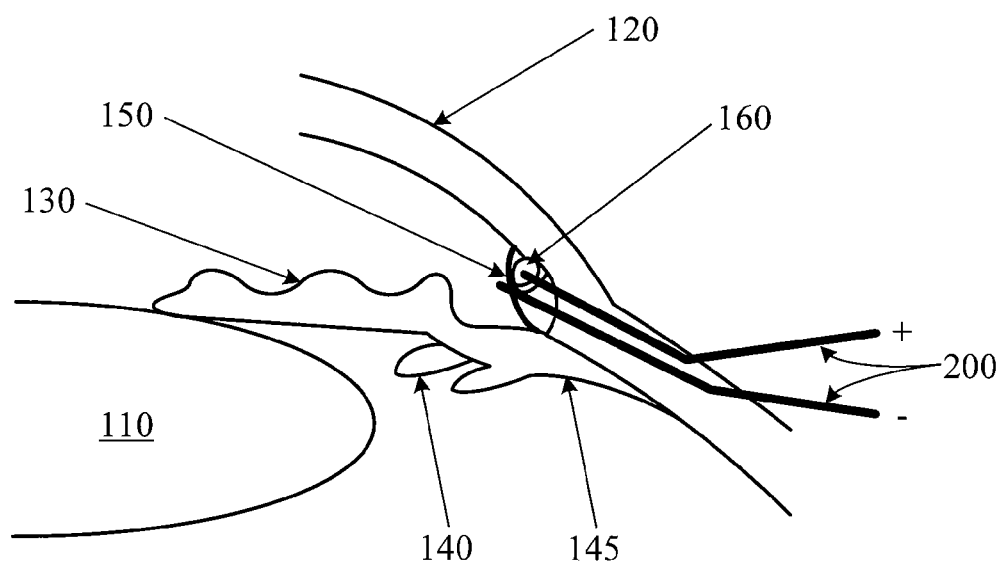
FIG. 2 is a diagram of the front portion of the eye with the treatment areas highlighted to explain a method of treating the eye consistent with the principles of the present invention.

FIG. 2 is a diagram of the front portion of the eye with the treatment areas highlighted to explain a method of treating the eye consistent with the principles of the present invention. In FIG. 2, representations of the lens 110, cornea 120, iris 130, ciliary bodies 140, ciliary muscle 145, trabecular meshwork 150, and Schlemm's canal 160 are pictured. In addition, a pair of electrodes 200 is located at the treatment site. The pair of electrodes 200 is located near the trabecular meshwork 150. In some cases, the electrodes 200 are generally located across the trabecular meshwork 150. However, they need not be. The electrodes 200 are located such that an electric field is generated in the vicinity of the trabecular meshwork 150, and more particularly in the juxtacanalicular region of the trabecular meshwork 150.

As noted, the trabecular meshwork 150 limits the outflow of aqueous. When this outflow is too limited, glaucoma can result. An extracellular matrix gel resides in the juxtacanalicular region of the trabecular meshwork 150. This extracellular matrix accounts for a significant portion of the resistance to aqueous flow. The extracellular matrix is made of proteoglycans (which in turn are made of glycosaminoglycans). Since glycosaminoglycans are negatively charged molecules, the application of an electric field across or near them causes them to migrate and/or reorient. The migration and/or reorientation of the glycosaminoglycans provides a reduction in flow resistance to aqueous that effectively lowers IOP.

A voltage applied across the electrodes 200 creates an electric field in the vicinity of the juxtacanalicular region of the trabecular meshwork 150 sufficient to cause migration and/or reorientation of the glycosaminoglycans. Since the thickness of the trabecular meshwork 150 in the vicinity of Schlemm's canal is about 100 microns, the spacing of electrodes 200 is preferably less than about one millimeter. Such a close spacing of electrodes 200 allows the application of a relatively high electric field with the application of moderate voltages and the consumption of very little power.

Numerous different electrode configurations are possible. For example, electrodes 200 may have sharp tips that serve to increase the strength of the generated electric field at the tips. Electrodes 200 may be oriented with respect to each other with an insulating part (not shown) that is attached to or integral with electrodes 200. Such an insulating part can serve to hold the electrodes 200 a particular distance apart (such as a distance less than one millimeter). In addition, the electrodes 200 can be individually encased in insulating material in order to limit the current flow through the intra-electrode space. The orientation, placement, and geometry of the electrodes 200 can be optimized so that the migration and/or reorientation of the glycosaminoglycans maximizes the cavities of the juxtacanalicular region of the trabecular meshwork 150 thereby minimizing the resistance to aqueous flow.

The voltage applied across the electrodes 200 may have any of a number of different temporal characteristics. For example, a constant (DC type) voltage can be applied so that a relatively constant electric field is present around the electrodes. The applied voltage may also be pulsed such that the voltage is turned on for a period of time and then turned off for a period of time. This pulsed voltage produces a similarly pulsed electric field at the electrodes 200. The pulsed electric field can be set at the resonant frequency of the extracellular matrix thereby facilitating the movement/reorientation of glycosaminoglycans. An AC-type voltage may also be applied so that the polarity of the field is reversed.

In one embodiment of the present invention, the electrodes 200 are contoured to the curvature of the trabecular meshwork, which represents a radius of curvature of approximately 6 mm. Typical electrode length is ideally 3 mm or less (but up to 13 mm) in order to span 30 degrees (or up to 120 degrees) of the angle. Electric field strength is typically between 500 and 5,000 Volts per centimeter. Thus, for a 1 mm electrode spacing, voltage applied is generally 50 to 500 V. The current passing through the electrode space will be approximately 1 to 10 microamps, for an applied power in the range of 0.5 to 50 milliwatts.

Figure 3:
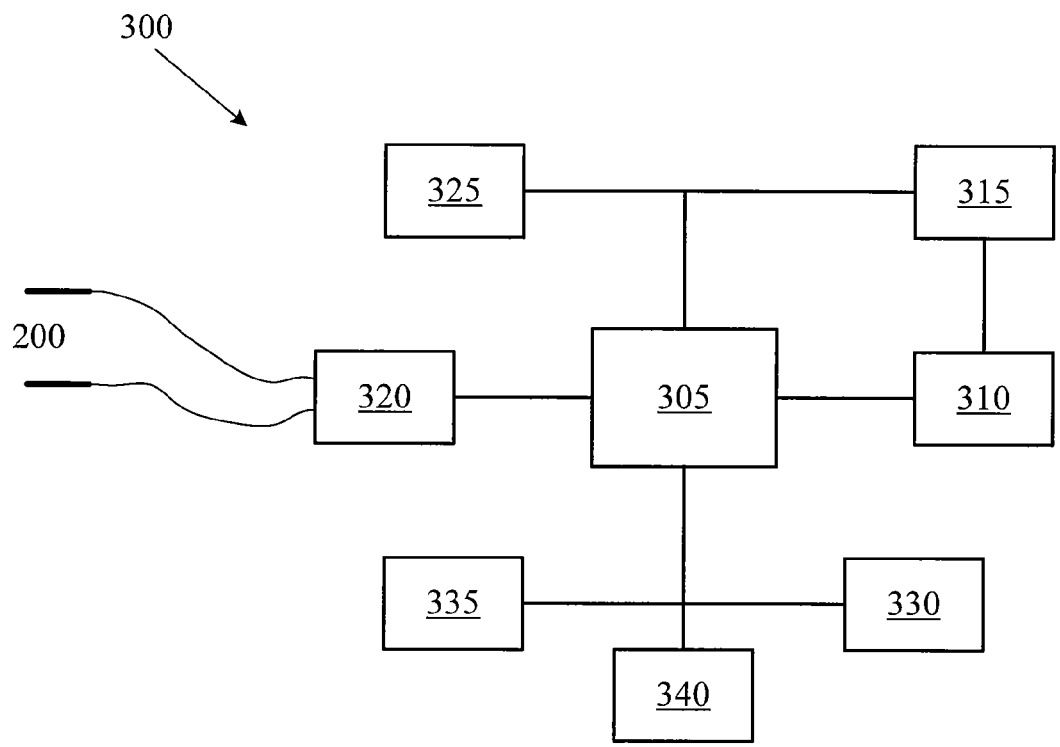
FIG. 3 is a block diagram of an electrical stimulation device according to the principles of the present invention.

FIG. 3 is a block diagram of an electrical stimulation device according to the principles of the present invention. In FIG. 3, electrical stimulation device includes a controller 305, a voltage source 310, recharge circuitry 315, output circuitry 320, pressure sensor 325, data transmission module 330, memory 335, optional speaker 340, and a pair of electrodes 200.

Controller 305 is typically an integrated circuit with power, input, and output pins capable of performing logic functions. In various embodiments, processor 305 is a targeted device controller. In such a case, controller 305 performs specific control functions targeted to a specific device or component, such as a voltage source 310, recharge circuitry 315, or output circuitry 320. In other embodiments, controller 305 is a microprocessor. In such a case, controller 305 is programmable so that it can function to control more than one component of the device. In other cases, controller 305 is not a programmable microprocessor, but instead is a special purpose controller configured to control different components that perform different functions.

Voltage source 310 is typically a rechargeable battery, such as a lithium ion or lithium polymer battery, although other types of batteries may be employed. In addition, any other type of power cell, such as a capacitor or an array of capacitors, is appropriate for voltage source 310. Voltage source 310 provides power to the device 300. Voltage source 310 can be recharged via an RFID link or other type of magnetic coupling via recharge circuitry 315.

Recharge circuitry 315 charges voltage source 310. In one embodiment of the present invention, recharge circuitry 315 utilizes inductive coupling to charge voltage source 310. When device 300 is implanted in the eye, such an inductive charging technique is particularly useful. When device 300 is an external device (as in FIG. 5), voltage source 310 can be recharged in any of a number of conventional ways.

Output circuitry 320 produces a voltage waveform that is applied across the pair of electrodes 200. Typically, output circuitry 320 produces pulses of voltage that are applied across the pair of electrodes 200. This pulsed voltage creates a pulsed electric filed that is provided in the vicinity of the trabecular meshwork.

Pressure sensor 325 is typically a small pressure sensor that is suitable for measuring an eye's intraocular pressure (IOP). Since elevated IOP is linked to glaucoma, pressure sensor 325 can provide an input to controller 305. In this manner, controller 305 can use IOP measurements from pressure sensor 325 to control the application of voltage to the electrodes 200. For example, if IOP is in a suitable range, then controller 305 may turn off the voltage applied to electrodes 200. If IOP is elevated, controller 305 may turn on voltage to the electrodes. Depending on the IOP measurement, controller 305 may direct a certain voltage level or type of pulsed voltage to be applied to electrodes 200. For example, the higher the IOP measured by pressure sensor 325, the higher the voltage applied to electrodes 200. Alternatively, in the case of a pulsed voltage, the time period during which the pulse is on can be increased or decreased based on the IOP reading from pressure sensor 325. Both the duration of the pulse and the voltage level of the pulse may be controlled by controller 305 based on the IOP reading of pressure sensor 325. The controller 305 can alter the voltage applied to the electrodes in numerous other ways based on a measured IOP.

Data transmission module 330 may employ any of a number of different types of data transmission. For example, data transmission module 330 may be active device such as a radio. Data transmission module 330 may also be a passive device such as the antenna on an RFID tag. In this case, an RFID tag includes memory 335 and data transmission module 330 in the form of an antenna. An RFID reader can then be placed near the system 300 to write data to or read data from memory 335. Since the amount of data typically stored in memory 335 is likely to be small, the speed with which data is transferred is not crucial. The types of data that can be stored in memory 335 and transmitted by data transmission module 330 include, but are not limited to, power source data (e.g. low battery, battery defect), speaker data (warning tones, voices), pressure sensor data (IOP readings, problem conditions), and the like.

Memory 335 is typically a semiconductor memory such as NAND flash memory. As the size of semiconductor memory is very small, and the memory needs of the system 300 are small, memory 335 occupies a very small footprint of system 300. Memory 335 interfaces with controller 305. As such, controller 305 can write to and read from memory 335. For example, controller 305 can be configured to read data from the pressure sensor 325 and write that data to memory 335. In this manner, a series of IOP readings can be stored in memory 335. Controller 305 is also capable of performing other basic memory functions, such as erasing or overwriting memory 335, detecting when memory 335 is full, and other common functions associated with managing semiconductor memory.

Optional speaker 340 provides a warning tone or voice to the patient when a dangerous condition exists. For example, if IOP is at a level that is likely to lead to damage or presents a risk to the patient, speaker 340 may sound a warning tone to alert the patient to seek medical attention or to administer eye drops. Controller 305 reads IOP measurements from pressure sensor 325. If controller 305 reads one or a series of IOP measurements that are above a threshold, then controller 305 can operate speaker 340 to sound a warning. The threshold can be set and stored in memory 335. In this manner, an IOP threshold can be set by a doctor, and when exceeded, a warning can be sounded.

Alternatively, data transmission module 330 may be activated to communicate an elevated IOP condition to a secondary device such as a PDA, cell phone, computer, wrist watch, custom device exclusively for this purpose, remote accessible data storage site (e.g. an internet server, email server, text message server), or other electronic device. In one embodiment, a personal electronic device uploads the data to the remote accessible data storage site (e.g. an internet server, email server, text message server). Information may be uploaded to a remote accessible data storage site so that it can be viewed in real time, for example, by medical personnel. In this case, the secondary device may contain the speaker 340. For example, in a hospital setting, after a patient has undergone glaucoma surgery and had system 300 implanted, a secondary device may be located next to the patient's hospital bed. Since IOP fluctuations are common after glaucoma surgery (both on the high side and on the low side which is also a dangerous condition), controller 305 can read IOP measurements made by an implanted pressure sensor 325. If controller 305 reads an unsafe IOP condition, data transmission module 330 can alert the patient and medical staff via speaker 340 or by transmitting the unsafe readings to a secondary device.

The pair of electrodes 200 is sized so as to fit in the vicinity of the trabecular meshwork, and preferably in the vicinity of the juxtacanalicular region of the trabecular meshwork. As such, the electrodes 200 are ideally 3 mm or less (but up to 13 mm) in length in order to span in the 30 degrees (or up to 120 degrees) of the angle and suitable for being spaced less than about a millimeter apart. As noted, an insulating part (not shown) may hold the electrodes in a particular configuration (e.g. the insulating part may hold the electrodes so that they are less than about one millimeter apart). In addition, the electrodes 200 can be individually encased in insulating material in order to limit the current flow through the intra-electrode space. Electrodes 200 can be of various shapes, with a preferred shape being high spatial divergences (sharpness) on one electrode and low divergence on the other (smoothness)—in order to maximize the intra-electrode electric field strength for a given electrode voltage difference and physical spacing. In one embodiment, the electrodes 200 are dielectric-coated, electrically-conductive wires in which high and low divergence are realized by relatively small and large wire diameters, respectively. For example, the wire diameter of the high-divergence electrode is 10 micrometers while that of the low-divergence electrode is 250 micrometers. Since the spacing of the electrodes 200 affects the characteristics and strength of the generated electric field, it is desirable to have the electrodes properly oriented with respect to each other (e.g. held at less than about one millimeter apart).

System 300 is preferably in a small, implantable, integrated package. As such, all of the components of system 300 can be built on a substrate, such as a semiconductor wafer, by any of a number of different processes.

Figure 4:
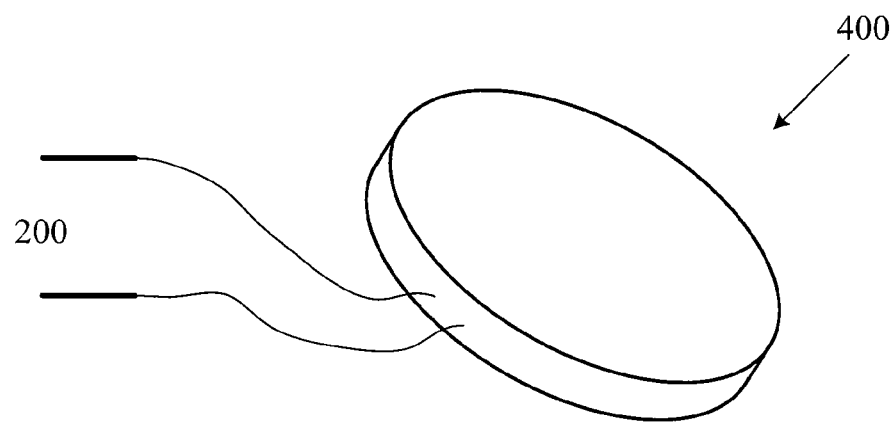
FIG. 4 is a perspective view of an implantable electrical stimulation device according to the principles of the present invention.

FIG. 4 is a perspective view of an implantable electrical stimulation device according to the principles of the present invention. The device of FIG. 4 may contain some or all of the components described in the block diagram of FIG. 3. In FIG. 4, the implantable stimulation device 400 is generally disc-shaped and conforms to the curvature of the eyeball. A pair of electrodes 200 is connected to the implantable stimulation device 400 via lead wires. Typically, the implantable stimulation device 400 has a sealed enclosure that is suitable for implantation in the eye. As such, the implantable stimulation device 400 may have a stainless steel case as an outer shell. The implantable stimulation device 400 is inserted under the conjunctiva near the limbus. Typically, the implantable stimulation device 400 is small—much less than the size of a dime.

From the above, it may be appreciated that the present invention provides a system for treating glaucoma. The present invention provides an electrical stimulation device that delivers a voltage to a pair of electrodes located in the vicinity of the trabecular meshwork. An electric field generated at the electrodes causes the glycosaminoglycans that make up the extracellular matrix to migrate and/or reorient thereby decreasing the resistance to the flow of aqueous. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating glaucoma in an eye having a juxtacanalicular region of a trabecular meshwork containing an extracellular matrix, the method comprising:

applying an electric field with a strength of between 500 and 5,000 Volts per centimeter in a vicinity of the juxtacanalicular region of the trabecular meshwork to cause migration or reorientation of glycosaminoglycans located in the extracellular matrix.

2. The method of claim 1 wherein the electric field is a pulsed electric field.

3. A method of treating glaucoma comprising:

providing a pair of electrodes coupled to a voltage source, the pair of electrodes having a spacing of less than one millimeter;

placing the pair of electrodes in the vicinity of the juxtacanalicular region of a trabecular meshwork; and applying a voltage of between 50 and 500 volts across the pair of electrodes sufficient to cause migration or reorientation of glycosaminoglycans located in the extracellular matrix.

4. The method of claim 2 wherein the voltage applied is a series of voltage pulses.

* * * * *